United States Patent [19]

Patel

[11] Patent Number: 4,883,485
[45] Date of Patent: Nov. 28, 1989

[54] EXPANDABLE LENS REPLACEMENT

[76] Inventor: Jayant K. Patel, 25 S. Raymond, #204, Alhambra, Calif. 91801

[21] Appl. No.: 50,084
[22] Filed: May 15, 1987
[51] Int. Cl.⁴ .............................................. A61F 2/16
[52] U.S. Cl. ........................................................ 623/6
[58] Field of Search ............................................ 623/6

[56] References Cited

U.S. PATENT DOCUMENTS 4,373,218  2/1983  Schachar ................................. 623/6
4,619,662  10/1986  Juergens, Jr. ........................... 623/6

FOREIGN PATENT DOCUMENTS 2124500  2/1984  United Kingdom .................... 623/6

*Primary Examiner*—Ronald L. Frinks
*Attorney, Agent, or Firm*—I. Michael Bak-Boychuk

[57] ABSTRACT

A method and apparatus for implanting synthetic lenses into a human eye in which the capsular bag is first evacuated of the natural lens substance and thereafter a peripheral spreader is inserted into the evacuated capsular bag within which an expandable lens sack is received. In one alternative the spreader forms the exterior position of the lens and is thus inserted as a collapsed structure into the capsular bag and in the other alternative the spreader comprises a plurality of arcuate segments expelled through a needle into the lens capsule.

5 Claims, 2 Drawing Sheets

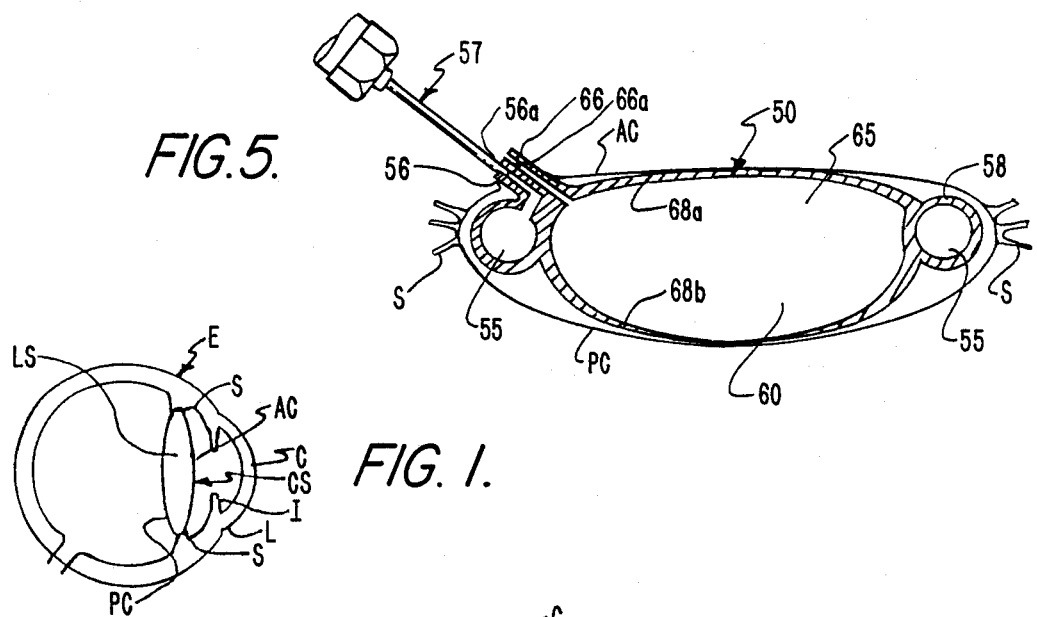
FIG. 5.
FIG. 1.
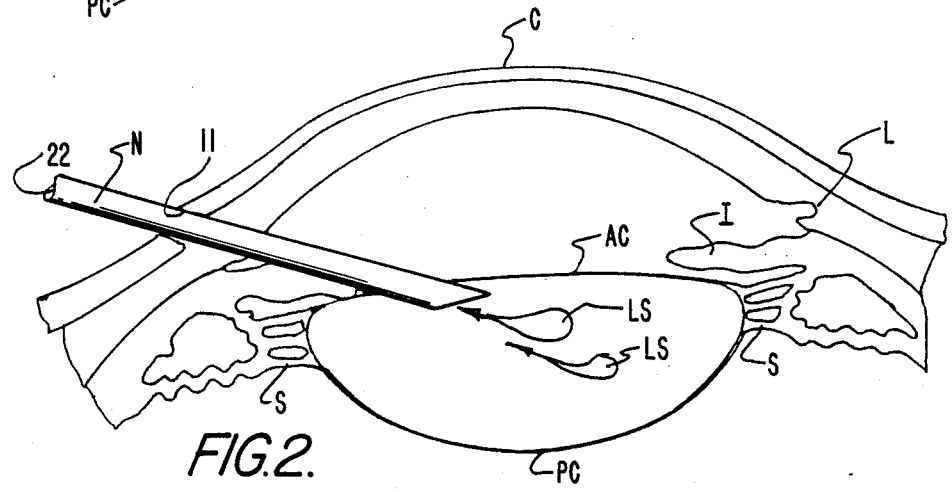
FIG. 2.
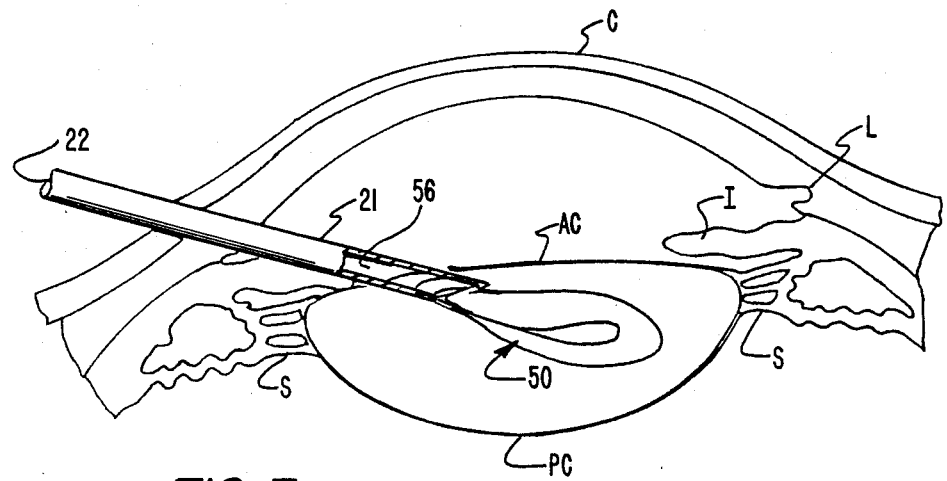
FIG. 3.

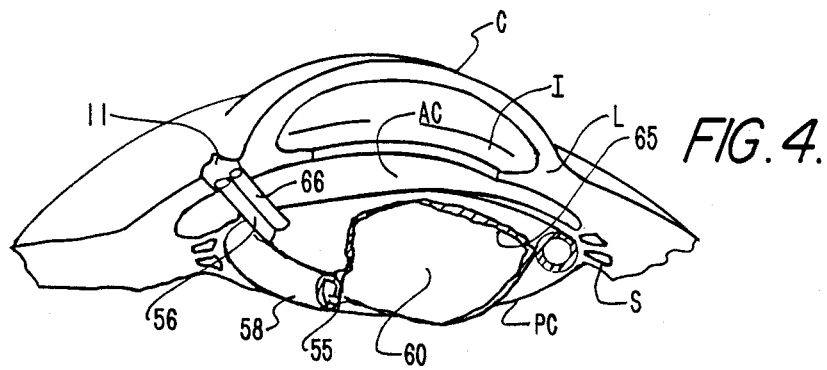
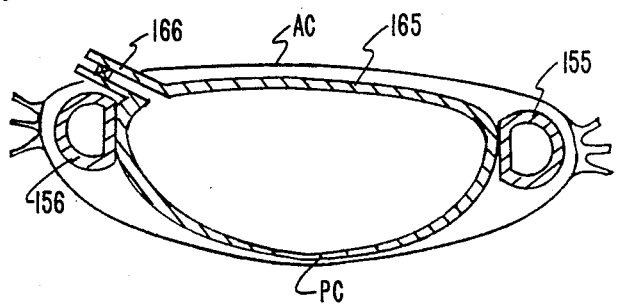
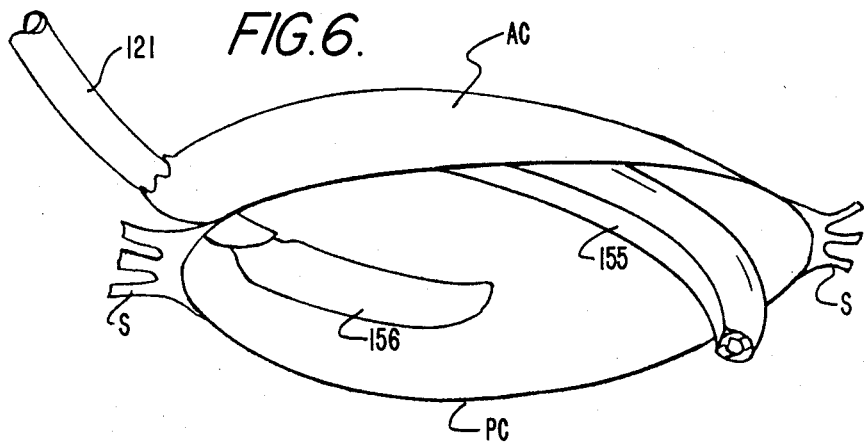
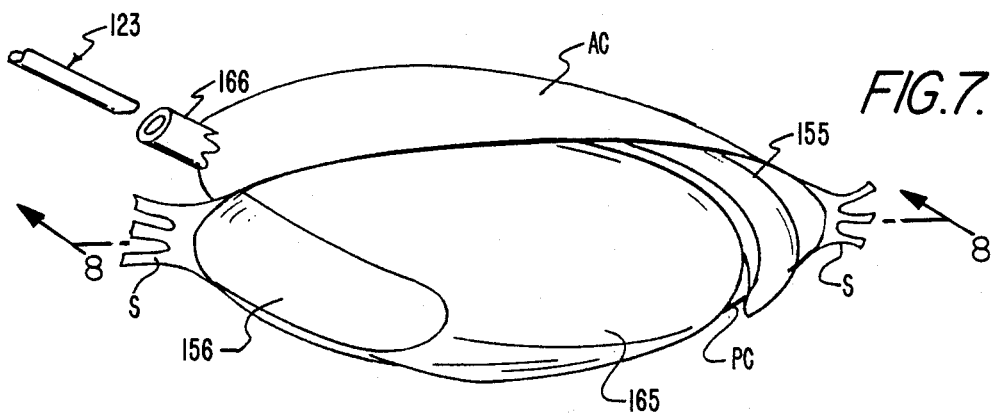

EXPANDABLE LENS REPLACEMENT

BACKGROUND OF THE INVENTION

1. Field of the Invention

The present invention relates to surgically inserted intraocular lenses, and more particularly to the apparatus and method for inserting liquid filled lenses into the natural capular bag of an eye.

2. Description of the Prior Art

Surgical implantation of synthetic intraocular lenses is a known practice in the treatment of optical diseases and is a method of preference in the treatment of cataract. Most typically the implanted lens is of a hard material (acrylic or silicon polymer) inserted in the ciliary sulcus or within the natural lens capsule of the eye after removal of the anterior capsule and the lens substance. While acceptable in many instances, a hard lens implant occasionally causes irritation.

While widely practiced, both the hard lens and the soft lens implants are large and thus entail extensive surgical incision with consequent extensive trauma. More importantly, lens shape, and position must be selected at the time of surgery and the lens must be securely fixed against movement. All these factors prompted alternative procedures, particularly procedures which permit post operative lens modification with minimal trauma.

One such procedure is described in U.S. Pat. No. 4,373,218 to Schachar. This procedure entails the insertion of an expandable sack into the cavity previously occupied by the lens capsule of the eye. A tube or neck projecting from the sack is then available for adding or withdrawing fluid which thus controls the inserted shape of the sack.

While suitable for the purposes intended this last procedure entails extraction of the natural lens capsule, an event coupled with unavoidable trauma, and the movement of vitreous liquid anterialy. Accordingly, less traumatic corrections of a diseased eye are extensively sought and it is one such technique that is disclosed herein.

SUMMARY OF THE INVENTION

It is, therefore, the general purpose and object of the present invention to produce a lens replacement technique which substantially retains the natural lens capsule and eliminates the need for a large surgical incision Other objects of the invention are to provide a technique for lens replacement with minimal trauma.

These and other purposes and objects are uniquely resolved by the instant technique which is best described by reference to the natural processes occurring in the eye. In the human eye the posterior and anterior lens capsules contain lens substance which occasionally is diseased, as in cataract, and thus is evacuated to restore full vision. When the lens substance is evacuated the intraocular fluid pressure collapses the anterior and posterior lens capsules into proximity which then causes natural regrowth of the lens substance. This regrowth commences dominantly in the capsular periphery and occassionally in other capsular locations. See "Lens Refilling and Regrowth of Lens Substance in the Rabbit Eye" by Julius Kessler M.D., Annals of Opthalmology, August, 1975 at pp 1059-1062. This regrowth of lens substance, furthermore, includes fibrous content which, while inconsequential to hard lens implants, produces some distortion with time to soft lens implants or the implants of fluid filled lenses. This regrowth effect is particularly pronounced in young patients.

Accordingly, the recent prior art suggests hard lens replacements which are some times anchored in place by peripheral ribs or radial extension as in U.S. Pat. Nos. 4,589,147 to Nevyas, 4,591,358 and 4,477,931 to Kelman and 4,073,014 to Paler. In each instance large and therefore traumatic incisions are necessary in the insertion procedure of the intraocular lens. Less invasive techniques, exemplified by the teachings of U.S. Pat. No. 4,542,542 to Wright, suggest the removal of the lens substance in the capsular bag and replacement by polymeric compositions which then cure in place. This procedure results in a lens implant of a shape defined by the capsular bag of the eye and the pressure at which the compositions are introduced.

To provide a minimally invasive lens replacement technique which is of a more predictable shape and which also allows for adjustment of the lens shape I have devised a method in which a captic or peripheral spreader is inserted into the evacuated capsular bag and within which an expandable sack is received. The expandable sack is then filled with clear fluid to pressure providing the lens shape by controlled expansion of shaped sack surfaces.

In one preferred form the sack and the peripheral spreader are parts of an expandable structure, the peripheral spreader forming a concentric, toroidal, cavity around the central sack. Both these expandable structures are formed of a resilient, collapsible, film which is rolled or folded and inserted into the evacuated capsular bag. Thereafter the peripheral spreader and sack volumes are separately expanded, the first to separate the anterior, equatorial and posterior capsules an the second to define the necessary optical shape.

Alternatively, the peripheral spreaders may be formed as arcuate segments insertable seriatium through a small opening into the capsular bag, the same opening being utilized for the insertion of the collapsed sack to minimize trauma.

In both implementations the sack material may be formed in distributed varying thickness which then controls the resulting lens shape by internal pressure. Moreover, expandable sacks may include ports, valves and/or filler extensions through which the internal fluid is injected.

In both forms the sack is implanted without the usual removal of the natural capsule bag the peripheral spreader then separating the anterior and posterior capsules to limit the problematic regrowth of lens substance. The procedure thus summarized minimized the operative trauma while controlling growth and at the same time permitting post surgical adjustments to the lens.

BRIEF DESCRIPTION OF THE DRAWINGS

FIG. 1 is a sectional view of a human eye useful in setting out the invention herein;

FIG. 2 is a sectional detail of the eye shown in FIG. 1 illustrating the initial step of the inventive procedure set out herein;

FIG. 3 is yet another sectional detail of the eye illustrating a further step of the inventive procedure;

FIG. 4 is a perspective illustration of the eye, in partial section, illustrating a first example of an implantable lens in accordance with the present invention;

FIG. 5 is a sectional view take along line 5—5 of FIG. 4;

FIG. 6 is yet another sectional detail, in perspective, illustrating an alternative implant sequence in accordance with the present invention;

FIG. 7 is a further sectional detail in the sequence shown in FIG. 6; and

FIG. 8 is a sectional view taken along line 8—8 of FIG. 7.

DESCRIPTION OF THE PREFERRED EMBODIMENTS

As shown in FIG. 1 the anatomical structure of a human eye E is characterized by a cornea C on the frontal segment of the limbus L extending over the variable aperture in the iris I. Below the iris I, suspended on ligaments (zonules) S is a capsular structure CS defined by an anterior capsule AC and a posterior capsule PC between which the clear lens substance LS is contained. Muscular contraction at the ligaments (zonules) S then, by tensile extension, modifies the shape of the lens capsules and thus modifies the optical path of the lens.

A variety of pathological processes are known which in one way or another affect the lens. Most prominent amongst these processes is cataract. The pathology of cataract involves the lens substance LS with a consequent reduction of optical functions through the lens.

Typically the effect of this disease is corrected by the removal of the lens including one or both capsular membranes. The function of the lens is then replaced either by a synthetic lens implant or by extremely thick and heavy glasses which must thereafter be consistently worn.

Heretofore techniques were devised for ultrasonic or mechanical withdrawal of the diseased lens substance from within the capsular bag. Typically, such withdrawal is by way of narrow instruments e.g., a syringe, illustrated in FIG. 2 by a syringe needle N. To evacuate the lens substance LS a narrow opening 11 is made in the cornea or limbus of the eye and through this opening the needle N is extended to pass through the anterior capsule AC. The lens substance LS is then evacuated from between the capsules.

In accordance with the present invention, following the evacuation of the lens substance LS, a second, somewhat larger, syringe needle 21, illustrated in FIG. 3, is inserted through opening 11. Of course, other tools, like a forcep, may be useful for the purpose herein. Needle 21 includes a central bore 22 in which a collapsed lens sack, generally at 50, is stored in a longitudinal, rolled column. A syringe 23, attached to needle 22, is then useful to expel the sack As shown in FIGS. 4 and 5 sack 50 may comprise two concentric cavities 55 and 65, cavity 55 formed as a toroidal, peripheral, tube around the central cavity 65. This concentric structure may be formed from a variety of resilient, biologically acceptable materials and may be provided with a resilient manifold, or tubular projections, 56 and 66 extending to communicate with cavities 55 and 65. When collapsed and folded for storage within needle 21 these tubular projections 56 and 66 are aligned rearmost, towards the syringe, within bore 22 and when the sack is expelled into the evacuated capsular bag formed by capsules AC and PC the projections 65 emerge towards the incision 11. In this position both cavities 55 and 65 may be selectively expanded by further injection of clear fluid from a fine tipped syringe 57 to the shape defined by the fluid pressure and the elastic coefficient of the sack walls.

By particular reference to FIGS. 4 and 5 the inserted sack 50, formed of an elastomer like clear polyethylene or silicon, includes the aforementioned peripheral cavity 55 extending about the central lens sack 65. Cavity 55 operates as a capsular spreader and thus its toroidal wall 58 is formed at a thickness sufficient for partial expansion by the elastic stiffness alone. Thus once expelled from the insertion needle 21 into the evacuated capsular bag the toroidal cavity 55 begins to uncurl and with the manipulative assistance by the attending physician, is positioned in the capsular bag for peripheral alignment. The lens sack 65, in turn, may comprise various wall thicknesses shown at 68a and b which, at pressure effect the desired lens shape. Accordingly, the tubular projections 56 and 66 are useful both to effect the positioning of the unexpanded sack 50 and thereafter for the injection of the internal fluid 60 once so positioned. For this purpose the projections may be provided with self-sealing orifices 56a and 66a or may be clamped off and sealed in place.

In the alternative, as shown in FIGS. 6-8, a plurality of arcuate, resilient spreader segments 155 and 156 may be inserted by expulsion from a syringe needle 121 into the evacuated capsular bag. To provide manipulative convenience needle 121 may be arced in the direction of the arc prestress of each segment 155 and 156. Once in position around the capsular periphery the spreaders then present a central cavity into which a lens sack 165, provided with a tubular projection 166, is received. This lens capsule, once again, may be stored in a syringe needle 123 to be expelled therefrom by syringe pressure, and when expelled is thereafter pressurized in the manner described above.

In both examples the peripheral juncture of the anterior and posterior capsules AC and DC is separated to limit the post operative regrowth of lens substance. This mechanical spreading of the capsular membranes for receipt of the lens sack is particularly useful since the natural capsular membranes are extremely thin and delicate and thus easily torn. The incidence of capsular tearing is thus reduced particularly with well rounded edges on the resilient inserts described herein.

Obviously, many modifications and changes may be made to the foregoing without departing from the spirit of the invention. It is therefore intended that the scope of the invention be determined solely on the claims appended hereto.

What is claimed is:

1. A method for implanting synthetic lenses into the natural capsular bag of a human eye, comprising the steps of:

making an incision in the said eye communicating into the interior of said capsular bag;

evacuating the natural lens substance from said capsular bag through said incision;

inserting a collapsed, expandable lens insert into a hollow needle, said lens insert including an exterior toroidal cavity formed at the periphery of a substantially circular lens cavity;

expelling said lens insert from said hollow needle through said incision into said evacuated capsular bag;

pressuring by injecting liquid under pressure into said torroidal cavity; and expanding by liquid pressure said lens cavity.

2. A method in accordance with claim 1 wherein:

said toroidal cavity and said lens cavity each comprise resilient material structures, each further including elongate, hollow projections proximately aligned to extend from said capsular bag into said incision.

3. A method in accordance with claim 2 further comprising the steps of:

aligning said lens insert in said capsular bag in the course of expelling thereof the present said toroidal cavity thereof towards the periphery of said capsular bag.

4. A method for implanting synthetic lenses into the natural capsular bag of an eye comprising the steps of:

forming an incision in said eye to communicate from the exterior thereof into said capsular bag evacuating the natural lens substance from said capsular bag through said incision;

inserting a corresponding resilient spreader segment into a hollow needle, said spreader sequencer being of an elongate configuration and pre-stressed to form an arc segment, when free, of an arc dimension substantially equal to the peripheral arc of said capsular bag;

expelling sequentially a plurality of said segments into said capsular bag into a serial alignment adjacent the periphery thereof;

convolving a resilient lens sack of substantially circular planform into the interior of a tubular probe; and ejecting said lens sack into said capsular bag within said segments.

5. A method according to claim 4 comprising the further step of:

pressurizing said lens sack after the ejection thereof to a pressure selected for elastic expansion thereof.

* * * * *